United States Patent [19]

Kodera et al.

[11] 4,366,125
[45] Dec. 28, 1982

[54] STERILIZATION APPARATUS AND PROCESS UTILIZING SYNERGISTIC EFFECT OF COMBINING HYDROGEN PEROXIDE AND ULTRA-VIOLET-RAY STERILIZATION

[75] Inventors: Tokio Kodera, Fuchu; Masaru Hoshino, Tokyo; Kimiaki Hyakutome, Tokyo, all of Japan

[73] Assignee: Dai Nippon Insatsu Kabushiki Kaisha, Tokyo, Japan

[21] Appl. No.: 209,663

[22] Filed: Nov. 24, 1980

[30] Foreign Application Priority Data

Nov. 27, 1979 [JP] Japan ............................. 54-153157

[51] Int. Cl.³ ......................... A61L 2/10; A61L 2/22
[52] U.S. Cl. ................................. 422/295; 422/20;
422/24; 422/27; 422/31; 422/297; 422/299
[58] Field of Search ............... 422/20, 24, 27, 28, 422/31, 297, 299, 295, 32

[56] References Cited

U.S. PATENT DOCUMENTS

| | | | |
|---|---|---|---|
| 3,481,689 | 12/1969 | Rosdahl et al. | 422/20 X |
| 3,513,627 | 5/1970 | Doucette et al. | 422/24 X |
| 3,750,367 | 8/1973 | Barker et al. | 422/28 X |
| 3,854,874 | 12/1974 | Loliger et al. | 422/299 |
| 3,904,361 | 9/1975 | Egger | 422/27 |
| 3,933,428 | 1/1976 | Egger | 422/28 |
| 4,225,556 | 9/1980 | Lothman et al. | 422/28 |
| 4,289,728 | 9/1981 | Peel et al. | 422/28 X |

*Primary Examiner*—Barry S. Richman
*Attorney, Agent, or Firm*—Koda and Androlia

[57] ABSTRACT

A long sheet material to be sterilized is passed through an atmosphere of $H_2O_2$ mist of low concentration and of droplet particle size of approximately 10 microns at room temperature for approximately one second and is then irradiated for approximately one second with ultraviolet-ray lamps positioned to irradiate opposite surfaces of the sheet material each at a distance of approximately 20 mm therefrom, whereby the material is thoroughly sterilized as a result of the synergistic effect produced by the combination of these two sterilization steps.

4 Claims, 2 Drawing Figures

FIG. I

STERILIZATION APPARATUS AND PROCESS UTILIZING SYNERGISTIC EFFECT OF COMBINING HYDROGEN PEROXIDE AND ULTRA-VIOLET-RAY STERILIZATION

BACKGROUND OF THE INVENTION

This invention relates generally to techniques for sterilizing articles particularly sheet materials. More particularly, the invention relates to an apparatus and process for sterilizing materials in the form of long sheets or strips, such as packaging materials, which can be payed out from and taken up on rolls. More specifically, the invention concerns the sterilization of such sheet materials by utilizing a remarkable, heretofore unanticipated sterilization effect afforded by the combined use of $H_2O_2$, i.e., hydrogen peroxide, and a UV, i.e., ultraviolet, lamps.

In $H_2O_2$ sterilization as practiced heretofore, $H_2O_2$ at room temperature has been used in some instances, but since the sterilizing or germicidal power thus obtained is weak, this technique has been inadequate for full sterilization. For this reason, heated $H_2O_2$, which has a powerful sterilization effect, has been used in many cases.

In the use of heated $H_2O_2$, however, steam and gaseous $H_2O_2$ tend to leak out of the apparatus and give rise to environmental pollution, which has not been desirable for the operator.

Furthermore, since the $H_2O_2$ thus used is in liquid form, the sterilization is of the wet type, and a large-capacity drying step has been required, which has been a difficulty in the design of the apparatus. In addition, there has also been the possibility of some $H_2O_2$ remaining because of inadequate drying. Still another problem has been that the concentration of the $H_2O_2$ used principally for sterilization has been 35 percent in most cases, whereby caution was necessary in handling this $H_2O_2$.

On the other hand, sterilization of packaging materials by irradiation with a UV lamp is a dry-type sterilization, in which a drying step is unnecessary, whereby it is a simple and convenient method of great effectiveness in sterilization. However, even with the use of powerful UV lamps, a long irradiation time is required for thorough sterilization, and this long irradiation time has given rise to damaging of the packaging material, lowering of its heat-seal strength, and discoloration thereof.

Thus, these two sterilization methods, when carried out independently for thorough sterilization, have had advantages and drawbacks. There has been a need for overcoming these drawbacks.

SUMMARY OF THE INVENTION

In view of the above described circumstances, it is an object of this invention to provide an apparatus and process for thoroughly sterilizing long sheet materials without the accompaniment of the above described problems. This and other objects of the invention have been successively achieved by the use of the apparatus and process of the invention wherein, by the combined use of the sterilization effects of $H_2O_2$ and a UV lamp, thorough sterilization is carried out, with minimum deleterious effect, by educing and utilizing a resulting synergistic effect.

According to this invention in one aspect thereof, briefly summarized, there is provided a process for sterilizing a material which comprises, in sequence, a first step wherein a thin film of hydrogen peroxide of low concentration at room temperature is applied onto the outer surfaces of the material thereby to carry out presterilization, a second step wherein the outer surfaces of the material thus coated with the hydrogen peroxide film are irradiated with ultraviolet rays, thereby being further sterilized, and a third step wherein the material thus irradiated is dried with aseptic hot air.

According to this invention in another aspect thereof, briefly summarized, there is provided a sterilization apparatus comprising: a plurality of housings communicatively connected in sequence and enclosing respective aseptic chambers which are constantly under positive pressure and adapted to permit the passage successively therethrough in one travel direction of a material to be sterilized; hydrogen peroxide sterilizing means in one of the housings for applying a thin film of hydrogen peroxide of low concentration at room temperature on the outer surfaces of the material thereby to carry out presterilization; ultraviolet-ray sterilizing means in a housing downstream in said travel direction from the hydrogen peroxide sterilizing means for irradiating said outer surfaces with ultraviolet rays; and drying means in a housing downstream from the ultraviolet-ray sterilizing means for drying the material with aseptic hot air.

The nature, utility, and further features of this invention will be more clearly apparent from the following detailed description with respect to a preferred embodiment of the invention as applied specifically to the sterilization of a packaging material when read in conjunction with the accompanying drawings briefly described below.

DETAILED DESCRIPTION OF THE INVENTION

Figure 1:
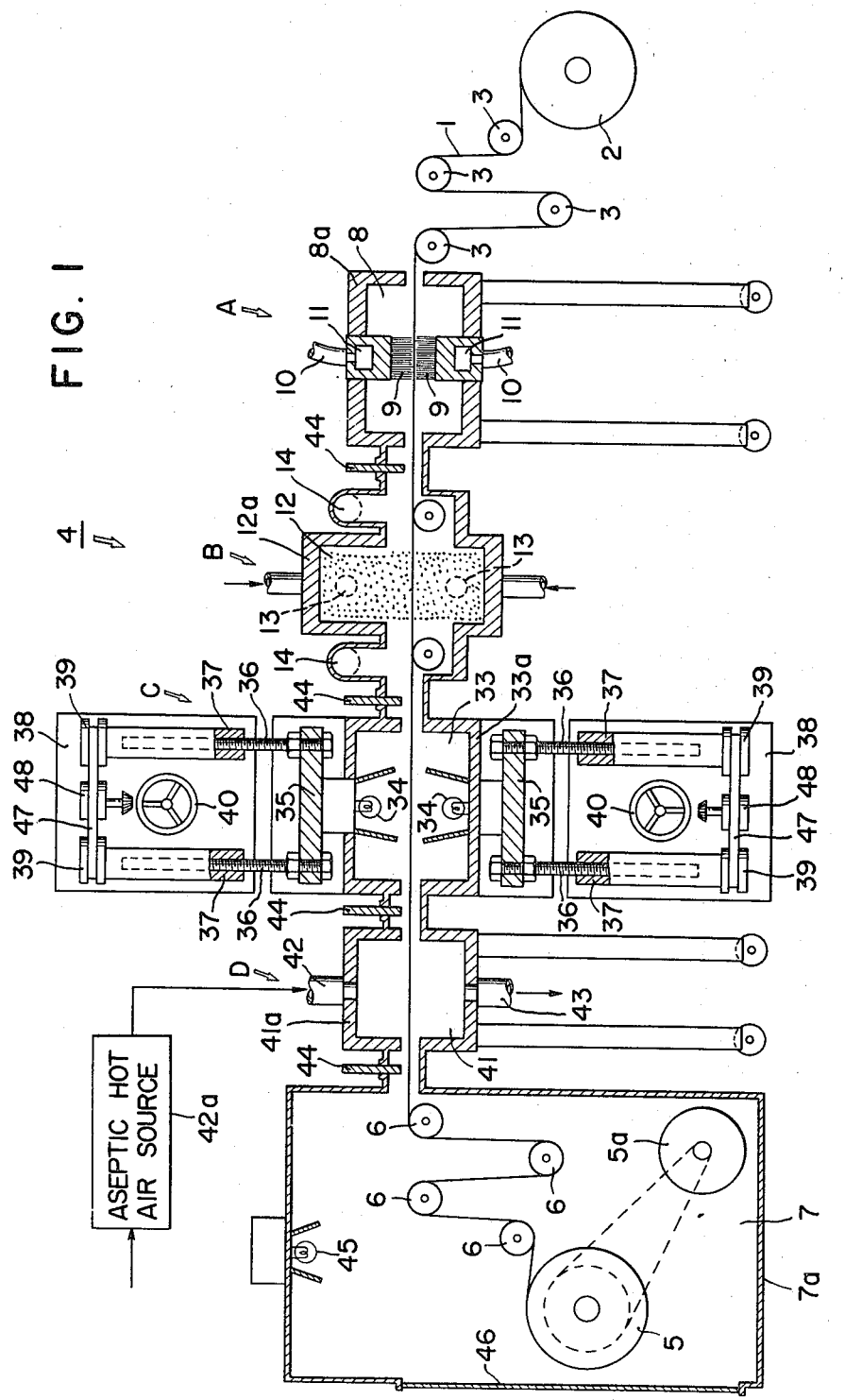
FIG. 1 is a schematic side view, with parts cut away and parts shown in longitudinal section, showing the essential parts and their arrangement in an example of a sterilization apparatus according to this invention.

Referring first to FIGURE 1, a packaging material 1 in the form of a long strip or sheet is drawn from a feed roll 2, caused to pass over and partially around guide rollers 3, and fed into a line of processing sections or devices. Then, after passing through a number of these processing devices as described hereinafter, the packaging material 1 enters a final take-up chamber 7 within a housing 7a, where it is passed around guide rollers 6 and taken up on a tape-up roll 5 driven by a motor 5a.

During this travel from the guide rollers 3 to the guide rollers 6, the packaging material 1 passes successively through a cleaning device A for brushing the opposite surfaces of the packaging material thereby to remove dust and dirt therefrom, an $H_2O_2$ device B for causing $H_2O_2$ mist of low concentration at room termperature to adhere to both surfaces of the packaging material, a UV device C for irradiating both surfaces of the packaging material with UV rays, and a drying device D for sterilizing and drying the packaging material with aseptic heated air.

The cleaning device A comprises essentially a dust-removal chamber 8 defined by a housing 8a having upstream and downstream walls respectively with inlet and outlet slits for passage of the packaging material 1, two brush devices 9 disposed in the middle part of the chamber 8 for brushing the opposite surfaces of the packaging material, and casings defining suction chambers 11 and fixedly mounted in opposite lateral walls of the housing 8a, the brush devices 9 being respectively mounted on the inner faces of these suction chamber casings. Suction pipes 10 connected to an outside suction source (not shown) are communicatively connected respectively to the suction chambers 11.

Accordingly, the opposite surfaces of the packaging material 1 are brushed by the brush devices 9 as the packaging material travels therebetween, and the dust particles adhering by electrostatic attraction to the packaging material are removed. The dust particles thus removed are drawn into the suction chambers 11 and, being sucked through the suction pipes 10, are discharged to the outside.

As an alternative to the removal of dust by suction, the method of sweeping the dust off the surfaces of the packaging material by blowing air thereagainst may be resorted to. In any case, the removal of dust adhering to the packaging material surfaces in the dust-removal chamber 8 serves to promote the sterilization. Depending on the necessity, an observation window may be provided in a wall of the housing 8a to afford observation of the dust-removal step in the chamber 8.

The succeeding device B for causing $H_2O_2$ mist of low concentration at room temperature to adhere to the two surfaces of the packaging material 1 has a mist atmosphere chamber 12 which is defined by a housing 12a, and through the middle part of which the packaging material travels. Mist-supplying pipes 13 are provided to supply the $H_2O_2$ mist into the mist chamber 12 respectively on opposite sides of the packaging material.

Figure 2:
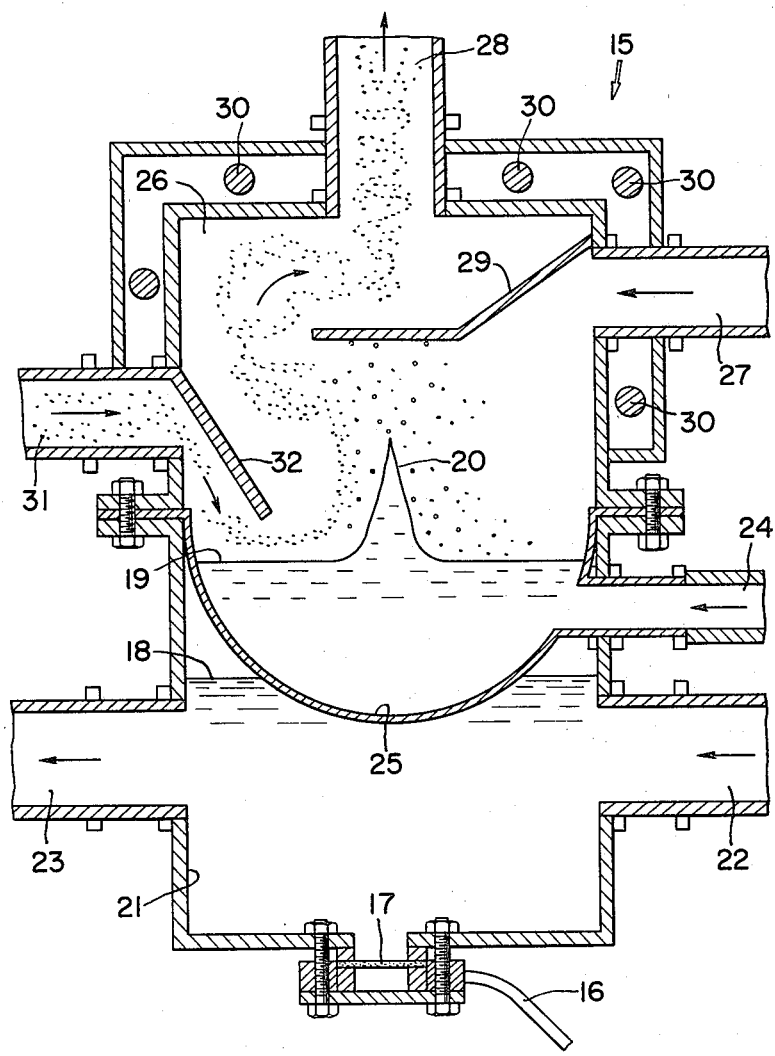
FIG. 2 is a relatively enlarged elevation, in vertical section, of an example of a device for atomizing a germicidal liquid into a mist for use in the apparatus illustrated in FIGURE 1.

The $H_2O_2$ mist to be thus supplied through the pipes 13 into the mist chamber is produced by ultrasonic waves generated by a sterilization or germicidal liquid atomizing device as, for example, the device 15 shown in FIG. 2. More specifically, an ultrasonic wave vibrator 17 mounted on the bottom of a tank 21, described hereinafter, is caused to undergo resonation by an ultrasonic wave oscillation circuit (not shown) connected to the vibrator by a coaxial cable 16 and thereby generates ultrasonic waves. These ultrasonic waves are propagated through warm water 18 as a propagation medium to a germicidal liquid 19 thereby to produce a mist of this liquid. Since the ultrasonic vibrator 17 is easily damaged by the sterilization liquid, its ultrasonic waves are propagated via the warm water 18. The oscillation frequency of the ultrasonic waves thus generated is, for example, 1.0 MHz to 2.0 MHz.

The germicidal liquid 19 thus acted upon by the ultrasonic waves is induced by the dispersive action thereof to assume a spire-like form 20 resembling that of water in a waterspout and, further, the form of a fog, that is, an $H_2O_2$ mist of low concentration at room temperature. Most of the droplet particles of this mist are substantially of the same size and, moreover, are very minute, being approximately 10 microns in diameter.

The warm water 18 in this device is pure water containing no impurities so as to facilitate its atomization and is held in a lower basin 21. This warm water 18 is constantly circulated through a water tank, a heating element, a cooler, and a pump (not shown), entering and leaving the lower basin 21 through a supply inlet 22 and a discharge outlet 23, respectively.

The germicidal liquid 19 is held in an upper basin 25, the bottom of which is immersed in the warm water 18 in the lower basin 21. The upper basin 25 is supplied with the germicidal liquid from a tank and through a heating element (both not shown) and an inlet pipe 24.

The above mentioned mist of the germicidal liquid is formed almost continuously in a chamber 26 above the liquid germicide in the upper basin 25 and, wafted and carried by a current of aseptic air heated by a heating element (not shown) and entering the chamber 26 through an inlet pipe 27, passes out of the chamber 26 through a discharge pipe 28 at the top part thereof to be conducted by the aforementioned mist-supplying pipes 13 into the mist atmosphere chamber 12 of the $H_2O_2$ device B. During this movement of the mist in the chamber 26, it is caused to travel through a zig-zag path around a selection plate 29 which is in the form of a baffle plate and functions to remove excessively large droplets of the mist.

Furthermore, the chamber 26 is provided therearound with heating means 30, by which the rising mist is constantly kept warm. To the chamber 26 at one side thereof is connected a return pipe 31 through which mist discharged from the mist chamber 12 of the $H_2O_2$ device B through the mist-exhaust pipes 14 is returned into the chamber 26. A deflecting and shielding plate 32 is disposed over the entrance of the return pipe into the chamber 26 to prevent reverse flow of the mist into the return pipe 31.

The UV device C has a UV irradiation chamber 33 within a housing 33a, which is provided with upstream and downstream slits through which the packaging material 1 from the mist chamber 12 is passed. UV lamps 34 are provided in the UV irradiation chamber 33 at positions to project UV rays onto respectively opposite surfaces of the packaging material 1 passing thereby. These UV lamps 34 are mounted at their bases on respective mounting heads 35 in symmetrically opposed state on opposite sides of packaging material at positions outside of the housing 33a.

Each mounting head 35 is, in turn, supported on the inner ends of parallel screw rods 36 screw engaged with respective tapped cylinders 37, the centerlines of these screw rods 36 and tapped cylinders 37 being substantially perpendicular to the line of travel of the packaging material 1. The tapped cylinders 37 associated with each mounting head 35 are mounted on a respective frame 38 in a manner such that they can rotate freely about their respective axes at specific positions relative to the frame 38. The tapped cylinders 37 thus rotatably mounted on each frame 38 are synchronously intercoupled by a mechanism comprising elements such as pulleys 39 respectively fixed to the cylinders 37 and an endless belt 47 passed around the pulleys 39 as well as a driving pulley 48. The driving pulley 48 is rotatably supported on each frame 38 and adjustably rotated by a handle 40 through a gear mechanism (not shown).

Thus, by rotating the handle 40 and thereby rotating the pulley 48, the pulleys 39, and the tapped cylinders 37, the screw rods 36 are extended or retracted, whereby the mounting head 35 and the UV lamp 34 mounted thereon are moved toward or away from the packaging material 1. In this manner, the UV lamps 34 on opposite sides of the packaging material 1 can be adjusted to a suitable distance from the material 1 for irradiating the same with UV rays for sterilization of the two surfaces thereof. This irradiation can be carried out with the UV lamps 34 positioned at a distance of approximately 20 mm from the surface of the material 1.

From the UV device C, the material 1 enters a sterilization and drying chamber 41 enclosed by a housing 41a of the drying device D. The housing 41a is also provided with upstream and downstream slits through which the material 1 enters and leaves the chamber 41. The housing 41a is provided at one lateral position thereof with an inlet pipe 42 for aseptic hot air supplied from an aseptic hot air source 42a. The aseptic hot air thus entering the chamber 41 sterilizes and dries the two surfaces of the material 1 and is exhausted from the chamber 41 through a discharge pipe 43.

Shield plates 44, functioning as glands, are provided at joints between the housings of adjacent devices A, B, C and D and the take-up chamber 7 to prevent or greatly reduce leakage of dust-laden air, $H_2O_2$ mist, and hot air from the various chambers of these devices into the adjacent chambers. These shield plates 44 are adapted to be adjustable, in the manner of gate valves, toward and away from the material 1 in order to conform to the nature of the material 1 which may range from an ordinary sheet material as illustrated to a sheet material formed with recesses serving as containers.

After being thus sterilized and dried in the drying device D, the material enters the take-up chamber 7. This take-up chamber 7 is provided on a part (upper wall part as viewed in FIGURE 1) thereof with a UV lamp 45 and in a wall part thereof near the take-up roll 5 with a door 46 for taking out the aseptic roll 5 after it has been fully wound.

Thus, in the sterilization apparatus of the above described construction according to this invention, the packaging material 1 is drawn out from the feed roll 2; is cleansed of dust in the dust-removal chamber 8; is passed through an atmosphere of $H_2O_2$ mist in the mist chamber 12, where the $H_2O_2$ mist of low concentration at room temperature is caused to adhere thereto; is passed, directly without being intentionally dried, into the irradiation chamber 33, where its two surfaces are irradiated by the opposed UV lamps 34 and thus sterilized; is dried in the sterilization and drying chamber 41 by aseptic hot air; and is wound into an aseptic roll material in the take-up chamber 7. Instead of being wound up into a roll, the sterilized and dried material 1, upon leaving the sterilization and drying chamber 41, can be fed directly to forming means and thereby formed into an article, or it can be fed to a bag-making machine.

As described hereinbefore, the $H_2O_2$ mist of low concentration at room temperature is produced by ultrasonic waves and comprises droplet particles of a particle size of the order of 10 microns. The above described process wherein this mist is caused to adhere to both surfaces of the material 1 is preferable to the application of the germicidal liquid by means of an ordinary spray nozzle since, in contrast, the spray particle size is large, and there is a possibility of the drying being inadequate and giving rise to difficulties. Furthermore, the drying in the sterilization and drying chamber 41 is accomplished almost instantaneously since the quantity of the fine droplets of the mist adhering to the surfaces of the material 1 is of an order of 10 microns such as to merely cause clouding of the surfaces, and since the $H_2O_2$ adhering to the surfaces of the material 1 is decomposed by the UV ray irradiation. Accordingly, large and elaborate drying equipment is unnecessary.

Actual tests were carried out by using a sterilization apparatus of the above described construction and operation. As a result, it was found that it is possible to accomplish thorough sterilization against Bacillus Subtilis of a concentration of $10_6/100$ $cm^2$ with a time for passage of the material 1 through a mist atmosphere zone of an $H_2O_2$ concentration of the order of 5 percent within 1 second and a UV irradiation time also within 1 second. For comparison, equivalent tests were carried out respectively with each of the two sterilization carried out independently. As a result, it was found that sterilization with a time of passage of 10 seconds through only the $H_2O_2$ mist is inadequate and that with a time of 10 seconds of UV irradiation is also inadequate.

From these test results, it may be concluded that the combination of the sterilization by means of $H_2O_2$ mist and that by means of UV ray irradiation, as afforded by the sterilization apparatus of this invention, produces a highly synergistic sterilization effect which is far greater than the sum of the sterilization effects of the two methods carried out independently.

As a result of other tests, it was confirmed that the substitution of a tank containing $H_2O_2$ for immersion therein of the material 1 for the $H_2O_2$ mist chamber 12 produces a similar highly effective sterilization effect.

A corollary advantage arising from the above mentioned synergic sterilization effect is that the sterilization apparatus can be made compact, at least much shorter than an apparatus relying on UV ray irradiation only, which would require a long line of a great number of UV lamps for producing an equivalent sterilization effect.

As a further result of tests, it was found that when the sequence of the $H_2O_2$ mist step and the UV ray irradiation step, each of 1-second duration, was reversed, the sterilization result was inadequate, and only a sterilization effect which was an arithmetic sum of the effects of the two steps carried out independently was recognizable.

While this invention has been described with respect to one preferred embodiment thereof wherein it is applied to the sterilization of a packaging material, the invention is not thus limited in scope, being applicable to the sterilization of other kinds of articles such as medical or surgical products and materials which are required to be in an aseptic state.

We claim:
1. A sterilizing apparatus comprising:
a plurality of housings communicatively connected in sequence and enclosing respective aseptic chambers which are constantly under positive pressure and adapted to permit the passage successively therethrough in one direction of a material to be sterilized;
hydrogen peroxide sterilizing means in one of the housing for applying a thin film of hydrogen peroxide of low concentration at room temperature on the outer surfaces of the material thereby to carry out presterilization, said sterilizing means applying a mist of hydrogen peroxide onto the outer surface of the material in sufficient quantity to produce cloudiness and the mist comprises droplets of hydrogen peroxide of a particle size of approximately 10 microns, the hydrogen peroxide sterilizing means further comprising a vessel containing hy- drogen peroxide of low concentration at room temperature, an ultrasonic generator coupled to said vessel for generating a hydrogen peroxide mist in the housing for said hydrogen peroxide sterilizing means through which the material is caused to travel, and means forming a chamber containing an ultrasonic vibration propagation medium, said propagation medium-containing chamber being located between said ultrasonic generator and the bottom of said vessel, whereby said ultrasonic generator acts through said propagation medium to generate said mist without the generator directly contacting said hydrogen peroxide;

ultra-violet-ray sterilization means in a housing downstream in said travel direction from the hydrogen peroxide sterilizing means for irradiating said outer surface with the hydrogen peroxide film thereon with ultra-violet-rays; and drying means in a housing downstream from the ultra-violet-ray sterilizing means for drying the material with aseptic hot air.

2. A sterilization apparatus according to claim 1 in which the ultraviolet-ray sterilizing means comprises at least two ultraviolet-ray lamps which are disposed on respectively opposite sides of the material passing thereby and adjustable in position relative to the material.

3. A sterilization apparatus according to claim 1, which is adapted to sterilize a long sheet material and comprises a feed roll for paying out the sheet material and a take-up roll for taking up the sheet material after being dried in the drying means.

4. A sterilizing apparatus according to claim 1, in which the propagation medium is warm water.

* * * * *